US006382831B1

(12) United States Patent
Bacchetta et al.

(10) Patent No.: US 6,382,831 B1
(45) Date of Patent: May 7, 2002

(54) INTRAORAL RADIOGRAPHIC FILM PACKET HOLDER WITH COMFORT ENHANCING EDGE

(75) Inventors: Richard W. Bacchetta; Scott H. Schwallie, both of Rochester; David C. Allen, Penfield, all of NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/534,393

(22) Filed: Mar. 24, 2000

(51) Int. Cl.[7] ................................................ A61B 6/14
(52) U.S. Cl. ...................... 378/170; 378/167; 378/168; 378/169; 378/170
(58) Field of Search ................................ 378/167, 168, 378/169, 170

(56) References Cited

U.S. PATENT DOCUMENTS

| | | |
|---|---|---|
| 1,537,925 A | 5/1925 | Bolin |
| 1,631,497 A | 6/1927 | Marler |
| 2,084,092 A | 6/1937 | Kenney |
| 4,626,216 A | 12/1986 | Strong-Grainger |
| 4,791,657 A | 12/1988 | Kirsch et al. |
| 4,805,201 A | 2/1989 | Strong-Grainger |
| 4,847,884 A | 7/1989 | Dove |
| 4,852,143 A | 7/1989 | Scheier et al. |
| 4,911,871 A | 3/1990 | Liese, Jr. |
| 4,912,740 A | 3/1990 | E. W. Liese |
| 4,913,288 A | 4/1990 | Tanaka |
| 4,922,511 A | 5/1990 | Gay |
| 5,044,008 A | 8/1991 | Jackson |
| 5,077,779 A | 12/1991 | Steinhausen, Jr. |
| 5,170,423 A | 12/1992 | Yurosko |
| 5,285,491 A | 2/1994 | Muylle et al. |
| 5,289,522 A * | 2/1994 | Kanabar et al. ............ 378/170 |
| 5,784,433 A | 7/1998 | Higa |

FOREIGN PATENT DOCUMENTS

| | | |
|---|---|---|
| EP | 0564011 | 10/1993 |
| FR | 2627076 | 8/1989 |

OTHER PUBLICATIONS

U.S. application No. 09/534,368, Bacchetta et al., filed Mar. 24, 2000.
U.S. application No. 09/533,867, Bacchetta et al., filed Mar. 24, 2000.
U.S. application No. 09/534,372, Bacchetta et al., filed Mar. 24, 2000.
U.S. application No. 09/534,370, Bacchetta et al., filed Mar. 24, 2000.
U.S. application No. 09/533,868, Resch et al., filed Mar. 24, 2000.
U.S. application No. 09/534,392, Earnhart et al., filed Mar. 24, 2000.
U.S. application No. 09/534,516, Resch et al., filed Mar. 24, 2000.

* cited by examiner

Primary Examiner—Robert H. Kim
Assistant Examiner—T Barber
(74) Attorney, Agent, or Firm—Mark G. Bocchetti

(57) ABSTRACT

A reusable bite block/film packet holder is taught which includes comfort enhancing features for holding intraoral radiographic film packets therein and for proper positioning in a patient's mouth. The bite block/film packet holder includes a bite-block and a support bracket extending at an angle of about 90° from the bite-block. There is a slot in the bite-block immediately adjacent the support bracket for engaging an edge of an intraoral film packet inserted therein. A perimetric border at the peripheral edge of the support bracket has a generally rounded cross-sectional configuration and extends beyond the dimensions of the intraoral film packet inserted in the slot. Thus, the sharp, die-cut edges of the film packet are prevented from uncomfortably engaging the soft/sensitive tissues of a patient's mouth. Rather the rounded, soft-feeling perimetric border of the bite block/film packet holder is the contacting element.

10 Claims, 3 Drawing Sheets

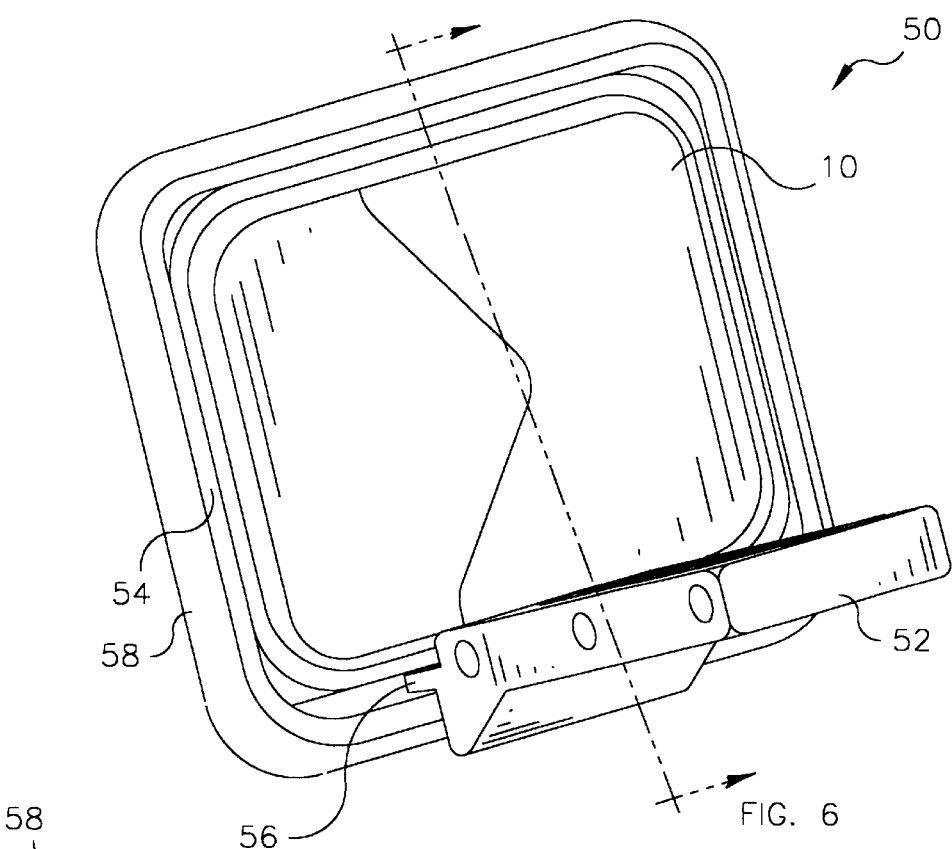
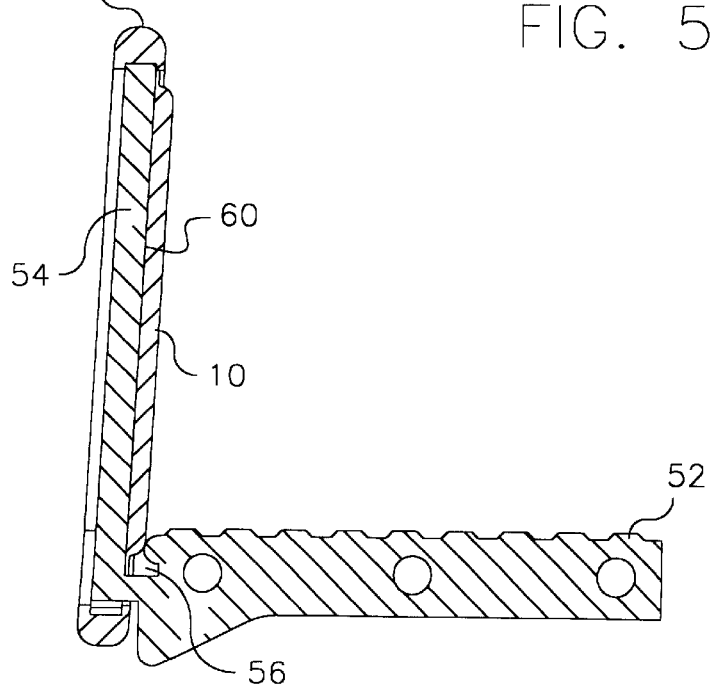
FIG. 5
FIG. 6

INTRAORAL RADIOGRAPHIC FILM PACKET HOLDER WITH COMFORT ENHANCING EDGE

FIELD OF THE INVENTION

The present invention relates generally to x-ray film packets and, more particularly, to bite block/film packet holders with comfort enhancing features for holding intraoral radiographic film packets and for proper positioning in a patient's mouth.

BACKGROUND OF THE INVENTION

A common problem experienced by people visiting the dentist is the discomfort and pain associated with the taking of dental x-rays caused by the positioning of intraoral radiographic film packets in the patient's mouth. The typical intraoral radiographic film packet includes relatively hard and/or relatively sharp edges that press against and irritate the gums and other oral soft tissue of the person whose teeth are being x-rayed. A variety of intraoral x-ray dental packets are known in the prior art which include features intended to be comfort enhancing. In addition, attempts have been made to create comfort-enhancing structures into which intraoral-x-ray dental packets can be inserted prior to placement in the patient's mouth. One example of this type of structure is taught in U.S. Pat. No. 5,044,008 titled "Dental Film Cartridge Cushion," by Reginald B. Jackson, Aug. 27, 1991. Jackson utilizes a cartridge cushion comprising a foam sheet sandwich into which the x-ray dental packet is placed for the purpose of cushioning and increasing the comfort to the patient. Jackson requires the manual insertion of the x-ray packet into the cartridge cushion. Thus, Jackson adds significant bulk to the packet and enhances the possibility of triggering a gag reflex action in the patient. Additionally, after the cartridge cushion is removed from the packet, it would be possible to reuse the cartridge cushion. Reuse without sterilization would not be sanitary and there is no practical way of sterilizing Jackson's cartridge which would not result in the destruction of the resilient foam and paper substrate thereof.

A second example of an add-on structure is taught in U.S. Pat. No. 5,285,491 titled "Dental Film Packet," by Wilfried Muylle et al., Feb. 8, 1994. Muylle et al. teaches sealing a film pack in an envelope consisting of a pair of thin pockets of injection molded plastic which are sealed with a band of adhesive tape. The envelope has no sharp edges and generally rounded corners. Thus, as with Jackson's device, this device requires manual insertion of the packet, adds significant bulk to the packet, enhances the possibility of triggering a gag reflex in the patient, and can also be reused in a non-sanitary manner.

U.S. Pat. No. 1,631,497 titled "Dental X-ray Film Package," by Harry L. Marler, Jun. 7, 1927, teaches a dental x-ray film package wherein a sensitized sheet is sandwiched between two opaque sheets. A heavy band of rubber is stretched about the periphery of the package to hold the package securely together and to provide the light tight joint.

U.S. Pat. No. 1,537,925 titled "Dental X-ray Film Package," by Leonard M. Bolin, May 12, 1925, teaches a dental x-ray film package wherein a pair of film sheets and the cover sheet are inserted into a container. The container consists of a frame including a backing portion in an enlarged continuous beading about the periphery thereof. The beading must be forced away from the backing portion and stretched peripherally in order to insert the film sheets and cover sheet therein. The container thus serves to hold the package together and provide the light seal.

U.S. Pat. No. 4,791,657 titled "Intraoral Radiographic Film Packet," by Alan Kirsch et al., Dec. 13, 1988, teaches a dental radiographic film packet which includes soft corners for greater patient comfort. The packet is constructed by removing all material from the corners of a typical dental radiographic film packet with the exception of the film chip. Individual corner covers which are seamless pockets are then added to the four corners of the packet. The corner covers create an airspace at each corner around the edge of the film chip.

U.S. Pat. No. 2,084,092 titled "Dental Film Holder," by Ralph Kenney, Jun. 15, 1937, teaches a dental film holder that is a stretchable vellum rubber plate with integral corner pockets into which an x-ray dental packet may be manually inserted. Kenney's dental film holder is intended to be reusable.

From the foregoing it can be seen that many attempts to add a comfort enhancing feature to dental x-ray film packets have resulted in structures requiring modification of individual film packets in order to receive a comfort enhancing structure. Further, such prior art attempts, particularly those seeking to provide the comfort enhancing feature via a frame, have resulted in a significant increase in bulk thereby enhancing the possibility of inducing a gag reflex.

SUMMARY OF THE INVENTION

It is therefore the object of the present invention to provide a reusable bite block/film packet holder with comfort enhancing features for holding intraoral radiographic film packets and for proper positioning in a patient's mouth.

It is a further object of the present invention to provide a bite block/film packet holder with comfort enhancing features which is reusable and sterilizable.

Yet another object of the present invention is to provide a bite block/film packet holder with comfort enhancing features into which a film packet can be easily inserted into a single engaging slot and which does not significantly increase the bulk of the film packet.

Still another object of the present invention is to provide a bite block/film packet holder which includes an abutting packet support with comfort enhancing features.

The foregoing and numerous other features, objects and advantages of the present invention will become readily apparent upon a review of the detailed description, claims and drawings set forth herein. These features, objects and advantages are accomplished by forming a plastic bite block/film packet holder including an bite-block with a support bracket projecting therefrom that about at 90 degree angle. There is an engaging slot in the bite-block immediately adjacent to the support bracket for receiving a side edge of an intraoral radiographic film packet. The dimensions of the support bracket are slightly larger than the dimensions of an intraoral radiographic film packet. Thus, when an intraoral radiographic film packet is inserted in the engaging slot, the edges of the support bracket project beyond the sharp, die cut edges of the film packet. The support bracket includes a soft perimetric border. When the film packet is placed into the bite block, its edges are internal to the soft edge of the bite block, and thus do not contact the soft tissues of a patient's mouth. Rather the soft border of the bite block is the contacting element. The bite block is preferably formed through injection molding of a thermoplastic material such as polypropylene. It is preferable that the material used for molding the bite block is sterilizable such as by autoclave, or cold liquid sterilization. In such manner, the bite block can be sterilized and reused from patient to patient. The soft perimetric border may be made from any one of a number of plastic materials with sufficiently a low durometer to present a soft feeling when placed in a patient's mouth. The shape of the perimetric border is generally rounded. Preferably, the perimetric border can also be sterilized and reused. The perimetric border may be integrally molded to the bite block, or be a separate element made similar to a rubber band and stretched over the edges of the face of the bite block, staying in place under tension. If the perimetric border is a separate element, it is preferable that such element be treated as disposable and not reused patient to patient. For example, a thermosetting material such as a silicone elastomer may be used to form the perimetric border, particularly if the perimetric border is a separate as oppose an integral element.

BRIEF DESCRIPTION OF THE DRAWINGS

FIG. 5 is a perspective view of an alternative embodiment reusable bite block/film packet holder embodiment to that shown in FIG. 2.

FIG. 6 is a cross-sectional view of taken along line 6—6 of FIG. 5.

DETAILED DESCRIPTION OF THE INVENTION

Figure 1:
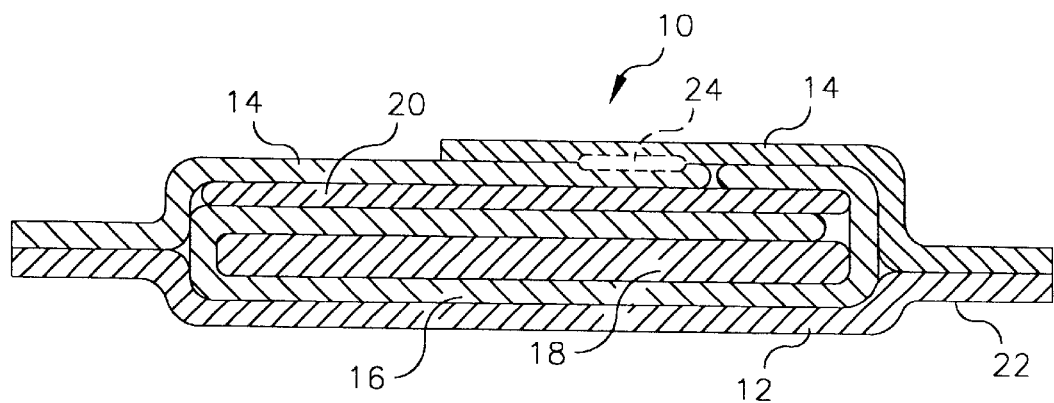
FIG. 1 is a cross-sectional view of a typical prior a dental film packet.

Turning first to FIG. 1, there is shown a cross-section of a typical prior art dental film packet 10. Dental film packet 10 includes an outer envelope comprising a polyvinyl chloride (PVC) sheet 12 on one face of the dental film packet 10 and a pair of overlapping PVC sheets 14 on the opposite face thereof. Contained between the sheet 12 and overlapping sheets 14 are a paper wrap element 16, a film chip 18 and a lead foil 20. PVC sheets 12 and 14 project beyond dimensions of the paper wrap element 16, the film chip 18 and lead foil 20 to yield a perimetric edge 22. Laminated perimetric edge 22 allows for heat sealing of PVC sheets 12 and 14 to one another to yield a light tight perimeter to the dental film packet 10. In addition, a heat seal (indicated by spot 24) is generated at the overlap of PVC sheets 14 to provide an outer envelope which is completely light tight and which is substantially watertight. This prior art dental film packet 10 therefore includes a relatively stiff and sharp perimetric edge created by the laminated perimetric edge 22. It is this relatively stiff and sharp perimetric edge which causes discomfort to the patient.

Figure 2:
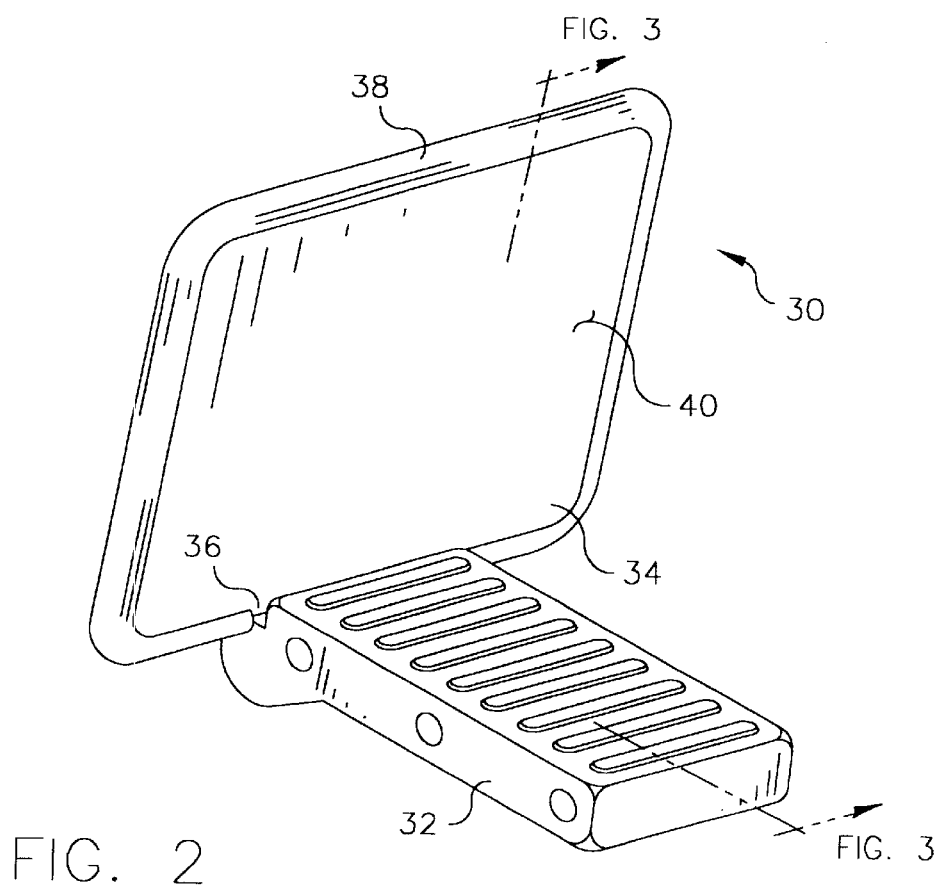
FIG. 2 is a perspective view of a reusable bite block/film packet holder embodiment of the present invention with comfort enhancing features for holding intraoral radiographic film packets therein.
Figure 3:
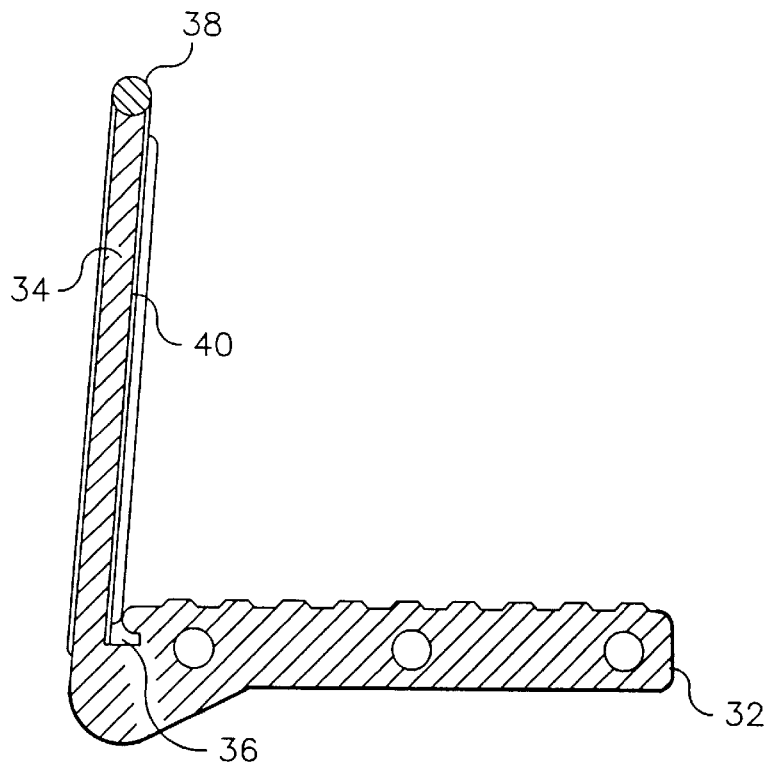
FIG. 3 is a cross-sectional view of a first embodiment wherein the perimetric border is integrally formed with the support bracket taken along line 3—3 of FIG. 2
Figure 4:
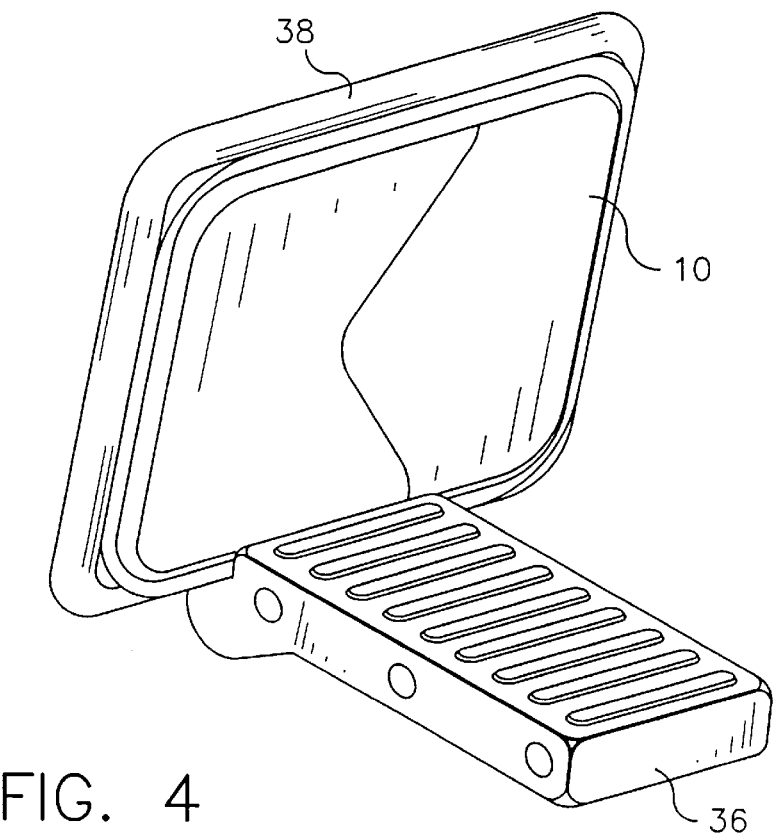
FIG. 4 is a perspective view of a reusable bite block/film packet holder embodiment of the present invention with an intraoral radiographic film packet therein.

Turning next FIGS. 2, 3 and 4, there is shown the first preferred embodiment of the bite block/film packet holder 30 of the present invention. The bite block/film packet holder 30 includes a bite-block 32 with a support bracket 34 extending at an angle of about 90° therefrom. Support bracket 34 has a generally rectangular configuration with rounded corners. Immediately adjacent to support bracket 34 there is a slot 36 formed in bite-block 32. Slot 36 is sized to frictionally engage a side edge of a film packet 10 inserted therein. Support bracket 34 includes a perimetric border or edge 38 integrally formed therewith. The perimetric border 38 includes a contiguous perimetric contact surface that has a generally rounded configuration in cross-section. The dimensions of support bracket 34 are such that when a film packet 10 is inserted into slot 36 the perimetric border 38 of support bracket 34 projects beyond the die cut edges of the film packet 10 as shown in FIG. 3. The film packet 10 is thus positioned such that PVC sheet 12 thereof abuts planar surface 40 of support bracket 34. In this manner, it is the soft-feeling, generally rounded perimetric border 38 that engages the oral tissues of the patient's mouth and not the sharp, die-cut edges of the film packet 10 that would irritate the soft/sensitive tissues inside a patient's mouth.

Bite block/film packet holder 30 is preferably formed by injection molding with a thermoplastic material such as, for example, polypropylene. Because it is preferable that the bite block/film packet holder 30 be reusable, it should be hard enough to prevent teeth marks. Although bite block/film packet holder 30 is preferably injection molded from a single material for ease and expense of manufacture, it can also be formed by co-injection molding two separate materials. The perimetric border 38 can be co-injection molded using the softer thermoplastic or thermosetting material such as PVC to enhance comfort while the remainder of the bite block/film packet holder 30 is co-injection molded with a thermoplastic material such as polypropylene.

Turning next to FIGS. 5 and 6 there is shown an alternative embodiment reusable bite block/film packet holder 50 of the present invention with comfort enhancing features for holding intraoral radiographic film packets therein. The bite block/film packet holder 50 includes a bite-block 52 with a support bracket 54 extending at an angle of about 90° therefrom. Support bracket 54 has a generally rectangular configuration with rounded corners. Immediately adjacent support bracket 54 to there is a slot 56 formed in bite-block 52. Slot 56 is sized to frictionally engage a side edge of a film packet 10 inserted therein. Support bracket 54 has a perimetric border or rim element 58 mounted thereon. The perimetric border or rim element 58 includes a contiguous perimetric contact surface that has a generally rounded configuration in cross-section. The dimensions of support bracket 54 are such that when a film packet 10 is inserted into slot 56 the perimetric border or rim element 58 of support bracket 54 projects beyond the die cut edges of the film packet 10. The film packet 10 is thus positioned such that PVC sheet 12 thereof abuts planar surface 60 of support bracket 54. In this manner, it is the soft-feeling, perimetric border or rim element 58 that engages the oral tissues of the patient's mouth and not the sharp, die-cut edges of the film packet 10 that would irritate the soft/sensitive tissues inside a patient's mouth. Perimetric border or rim element 58 is preferably similar in configuration to a rubber band such that it may be stretched over the perimetric edge of the support bracket 54, staying in place under tension. For example, a thermosetting material such as a silicone elastomer may be used to form the perimetric border or rim element 58. As depicted in FIGS. 5 and 6, perimetric border or rim element 58 is generally cylindrical with a longitudinal slot therein into which the peripheral edge of support bracket 54 is inserted. As such, perimetric border or rim element 58 is retained on a peripheral edge of support bracket 54 by tensioning of the perimetric border or rim element 58, or by friction, or by a combination of tension and friction. Alternatively, a true rubber band-like structure can be used. The elastomeric nature of such a structure would cause the rim element to deform and partially wrap about the peripheral edge of support bracket 54 to thereby result in a rim element having a generally rounded cross-sectional configuration.

Although the molded frames 30 and 50 are described herein as preferably being formed by an injection molding process, it should be recognized that other molding processes can also be used. For example, frames 30 and 50 can be molded using a casting process, a pressure forming process, or a thermoforming process.

Those skilled in the art will recognize that there are two versions of dental x-ray film packets. One is composed of layers of soft thermoplastic sheets between which film, cardboard and a lead barrier are sealed. A second version uses stiff paper for the outer envelope. The stiff paper version includes the same internal elements as the thermoplastic sheet version. Both of these versions can take advantage of this invention.

Those skilled in the art will also recognize that there are now digital radiography products available which are intended to be used in place of dental x-ray film packets. One example of this type of technology uses a plate that is coated with phosphorous. When exposed to radiation, the plate will create an image that can be scanned with a laser into a computer instead of being chemically processed. To the extent that these products have the same problems of patient discomfort, the present invention can be used to solve such problems. Similarly, intraoral products which use a CCD sensor array may also achieve some level of comfort benefit through the application of the present invention.

From the foregoing, it will be seen that this invention is one well adapted to obtain all of the ends and objects hereinabove set forth together with other advantages which are apparent and which are inherent to the apparatus.

It will be understood that certain features and subcombinations are of utility and may be employed with reference to other features and subcombinations. This is contemplated by and is within the scope of the claims.

As many possible embodiments may be made of the invention without departing from the scope thereof, it is to be understood that all matter herein set forth and shown in the accompanying drawings is to be interpreted as illustrative and not in an illuminating sense.

PARTS LIST

10 dental film packet (prior art)
12 outer envelope comprising a vinyl sheet
14 outer envelope comprising overlapping vinyl sheets
16 paper wrap element
18 film chip
20 lead foil
22 laminated perimetric edge
24 heat seal
30 bite block/film packet holder
32 bite block
34 support bracket
36 slot
38 perimetric border
40 planar surface
50 reusable bite block/film packet holder (present invention)
52 bite block
54 support bracket
56 slot
58 perimetric border or rim element
60 planar surface

What is claimed is:

1. A film packet holder for holding an intraoral film packet comprising:
   (a) a bite-block;
   (b) a support bracket extending at an angle of about 90° from said bite-block;
   (c) a slot in said bite-block immediately adjacent said support bracket for engaging an edge of an intraoral film packet inserted therein; and
   (d) a perimetric border about a peripheral edge of said support bracket, said perimetric border having a generally rounded cross-sectional configuration, said perimetric border extending beyond the dimensions of the intraoral film packet inserted in said slot, the intraoral film packet being retained in said film packet holder only by engaging said slot in said bite-block.

2. A film packet holder for holding an intraoral x-ray film packet as recited in claim 1 wherein:
   said bite-block, said support bracket and said perimetric border are all integrally formed.

3. A film packet holder for holding an intraoral x-ray film packet as recited in claim 1 wherein:
   said bite-block, said support bracket and said perimetric border are integrally formed by injection molding a thermoplastic material.

4. A film packet holder for holding an intraoral x-ray film packet as recited in claim 1 wherein:
   said bite-block and said support bracket are integrally formed, and said perimetric border is a separate, disposable element mounted on said peripheral edge of said support bracket and retained there by tension of said perimetric border.

5. A film packet holder for holding an intraoral x-ray film packet as recited in claim 1 wherein:
   said bite-block and said support bracket are integrally formed, and said perimetric border is a separate, disposable element mounted on said peripheral edge of said support bracket and retained there by friction.

6. A film packet holder for holding an intraoral x-ray film packet as recited in claim 1 wherein:
   said bite-block and said support bracket are integrally formed by injection molding a thermoplastic material, said perimetric border being a separate, elastomeric element mounted on said peripheral edge of said support bracket and retained there by friction.

7. A film packet holder for holding an intraoral x-ray film packet as recited in claim 1 wherein:
   said bite-block and said support bracket are integrally formed by injection molding a thermoplastic material, said perimetric border being a separate, elastomeric element mounted on said peripheral edge of said support bracket and retained there by tension of said perimetric border.

8. A film packet holder for holding an intraoral x-ray film packet as recited in claim 1 wherein:
   said bite block, said support bracket and said perimetric border are integrally formed by co-injection molding a thermoplastic material and an elastomeric thermoplastic.

9. A film packet holder for holding an intraoral x-ray film packet as recited in claim 1 wherein:
   said bite block, said support bracket and said perimetric border are integrally formed by co-injection molding a thermoplastic material and an elastomeric thermosetting material.

10. A film packet holder for holding an intraoral x-ray film packet as recited in claim 1 wherein:
    said bite-block and said support bracket are integrally formed, and said perimetric border is a separate, disposable element mounted on said peripheral edge of said support bracket and retained there by tension.

* * * * *